United States Patent
Hofmeister et al.

(10) Patent No.: US 9,562,862 B2
(45) Date of Patent: Feb. 7, 2017

(54) OPTICAL AND CHEMICAL ANALYTICAL SYSTEMS AND METHODS

(71) Applicant: H2Optx Inc., San Jose, CA (US)

(72) Inventors: Rudy Hofmeister, San Jose, CA (US);
Scott Tandy, Los Altos, CA (US);
Donald Ice, Milpitas, CA (US)

(73) Assignee: H2Optx Inc., San Jose, CA (US)

( * ) Notice: Subject to any disclaimer, the term of this patent is extended or adjusted under 35 U.S.C. 154(b) by 228 days.

(21) Appl. No.: 14/507,637

(22) Filed: Oct. 6, 2014

(65) Prior Publication Data
US 2016/0069805 A1    Mar. 10, 2016

Related U.S. Application Data

(60) Provisional application No. 62/048,180, filed on Sep. 9, 2014.

(51) Int. Cl.
*G01N 21/00* (2006.01)
*G01N 21/65* (2006.01)
*G01N 21/64* (2006.01)

(52) U.S. Cl.
CPC .......... *G01N 21/65* (2013.01); *G01N 21/6456* (2013.01)

(58) Field of Classification Search
CPC .............. G01N 21/65; G01N 21/64; G01J 3/44
USPC ..................................................... 356/72–73
See application file for complete search history.

(56) References Cited

U.S. PATENT DOCUMENTS

| | | | |
|---|---|---|---|
| 3,166,939 A | 1/1965 | Koeller et al. | |
| 4,900,435 A | 2/1990 | Anderson | |
| 5,096,471 A | 3/1992 | Sacks et al. | |
| 5,944,877 A | 8/1999 | O'Neil | |
| 7,928,370 B2 | 4/2011 | Amirav et al. | |
| 2007/0146701 A1* | 6/2007 | Kiesel | G01N 21/03 356/317 |
| 2008/0112853 A1* | 5/2008 | Hall | G01N 21/3577 422/82.05 |
| 2016/0041087 A1 | 2/2016 | Hofmeister et al. | |

OTHER PUBLICATIONS

International Search Report and Written Opinion mailed Nov. 6, 2015 for International Patent Application No. PCT/US2015/044264 filed Aug. 7, 2015.

* cited by examiner

*Primary Examiner* — Abdullahi Nur

(57) ABSTRACT

Optical and chemical analytical systems and methods are provided herein. In one embodiment, a method includes exposing a mixture sample to electromagnetic radiation, the mixture sample including analytes, detecting responsiveness of one or more of the analytes to the electromagnetic radiation, calculating average responsiveness of the one or more of the analytes, and calculating a concentration of the one or more of the analytes in the mixture sample using the average responsiveness.

16 Claims, 13 Drawing Sheets

Vitamin D Particle Size Model
| | |
|---|---|
| Observed Diameter | 200 microns |
| Calculated Radius | 100 microns |
| Calculated Projected Area | 31416 microns^2 |
| Calculated Volume | 4188790 microns^3 |
| Density PEG6000 | 1.08 g/cc |

Calcium Carbonate Model
| | |
|---|---|
| Density Calcium Carbonate | 2.71 g/cc |

Calculate Volume Percentages
| | |
|---|---|
| VitaminD Mass Percentage (aprox) | 0.1 % |
| Calcium Carbonate / Other % | 99.9 % |
| Density Ratio CC to D3 | 2.50925926 |
| Vitamin D Nominal Volume | 0.25092593 |
| Calcium Carbonate Nominal Volume | 99.9 |
| Total Reference Volume | 100.150926 |
| Vitamin D % by volume | 0.25054778 |
| Calcium Carbonate by Volume | 99.75 |

Calculate # of Vitamin D Particles on Well Floor Based on Simple Area Assumption
| | |
|---|---|
| Well Floor Area (4000*4000) | 16000000 microns^2 |
| Vitamin D Area based on Volume % | 40148 microns^2 |
| Vitamin D particles expected per well | 1.28 |

*FIG. 9*

OPTICAL AND CHEMICAL ANALYTICAL SYSTEMS AND METHODS

CROSS REFERENCE TO RELATED APPLICATIONS

This application claims the priority benefit of U.S. Provisional Patent Application Ser. No. 62/048,180, filed on Sep. 9, 2014, titled "OPTICAL AND CHEMICAL ANALYTICAL SYSTEMS AND METHODS", which is hereby incorporated by reference herein in its entirety, including all references cited therein.

FIELD OF THE INVENTION

The present technology is broadly directed to systems and methods that are used to evaluate products created in on-the-line manufacturing processes. For example, the present technology can be used for new product analysis and process debugging. The present technology can be used in manufacturing transition management as well as manufacturing monitoring and yield enhancement. The present technology can also be used in manufacturing process departure investigation and mitigation.

SUMMARY

According to some embodiments, the present technology is directed to a method for detecting a concentration of an analyte in a sample mixture. The method comprises: (a) exposing a mixture sample to electromagnetic radiation, the mixture sample comprising analytes; (b) detecting responsiveness of one or more of the analytes to the electromagnetic radiation; (c) calculating average responsiveness of the one or more of the analytes; and (d) calculating a concentration of the one or more of the analytes in the mixture sample using the average responsiveness.

According to some embodiments, the present technology is directed to a method comprising: (a) fluorescing a plurality of samples of CAVD; (b) for each of the plurality of samples of CAVD, locating analytes that fluoresce at 405 nm; (c) determining what part of the analytes are Vitamin D; and (d) calculate average fluorescence of the Vitamin D over the plurality of samples to determine the concentration of Vitamin D in the plurality of samples of CAVD.

According to some embodiments, the present technology is directed to a method comprising: (a) capturing high resolution color or monochrome images of a mixture sample of CAVD powder using multiple wavelengths of light, wherein the multiple wavelengths of light are directed to the mixture sample at different angles; (b) processing the high resolution images to identify possible Vitamin D particles by size, color, and shape; (c) conducting a Raman spectroscopic analysis of the possible Vitamin D particles to confirm identification of the Vitamin D particles; and (d) calculating a particle area to percentage-by-weight value where a percentage-by-weight is correlated to a percentage-by-area of Vitamin D particles observed in the high resolution images.

BRIEF DESCRIPTION OF THE DRAWINGS

Certain embodiments of the present technology are illustrated by the accompanying figures. It will be understood that the figures are not necessarily to scale and that details not necessary for an understanding of the technology or that render other details difficult to perceive may be omitted. It will be understood that the technology is not necessarily limited to the particular embodiments illustrated herein.

FIGS. 7-9 collective illustrate example calculations of Vitamin D concentration in CAVD samples, determined in accordance with the present technology.

DETAILED DESCRIPTION

In some embodiments, the present technology is directed to a method for detecting a concentration of an analyte in a sample mixture. In general, analytes are any constituent part of a sample mixture that can be measured quantitatively and/or qualitatively. The analysis methods described herein are advantageous in terms of efficiency and accuracy. These methods can be performed on sample mixtures obtained during batch manufacturing, where samples are obtained on the product production line at given periods of time. Each time a mixture sample is obtained and analyzed using one or more of the analysis methods described herein.

The products that can be analyzed with the methods and systems of the present technology include powders, liquids (including emulsions and suspensions), solids, and other similar homogeneous and/or heterogeneous combinations or compositions of materials. In some examples, the present technology can be used to detect particles in various compositions such as pharmaceuticals or other chemical compounds. More specifically, the present technology employs the use of electromagnetic radiation, and in some embodiments ranges of wavelengths (or a specific wavelength) of the electromagnetic radiation spectrum to excite a mixture sample. Various parts of a mixture sample, referred to hereinafter as analytes, will react to different wavelengths of the electromagnetic radiation spectrum.

These reactions can be measured and quantitatively analyzed to determine analyte size and shape. Also, a volume by weight of analyte can be determined for the mixture sample.

The present technology can also distinguish between different analytes in the same mixture sample, as well as contaminates that also react to the applied electromagnetic radiation spectrum.

In some embodiments, the present technology can be used to calculate an average responsiveness of one or more analytes to a wavelength or wavelengths of electromagnetic radiation.

Using the average responsiveness, the present technology can calculate a concentration of the one or more of the analytes in the mixture sample using the average responsiveness.

The present technology can use these processes to evaluate a plurality of mixture samples of a batch of mixture that is currently being manufactured. Thus, an average or aggregate of analyte volume for the batch can be approximated using the mixture samples.

For example, the present technology can be used to process a calcium supplement powder that comprises Vitamin D particles (hereinafter "CAVD") [one example is Caltrate™] or CAVD in pill form, to determine a concentration of Vitamin D in the CAVD powder. For context, it is advantageous to know the concentration of Vitamin D when manufacturing CAVD powder. If Vitamin D concentrations are not in accordance with manufacturing specifications, the batch of CAVD powder must be discarded causing a significant financial loss.

Figure 1A:
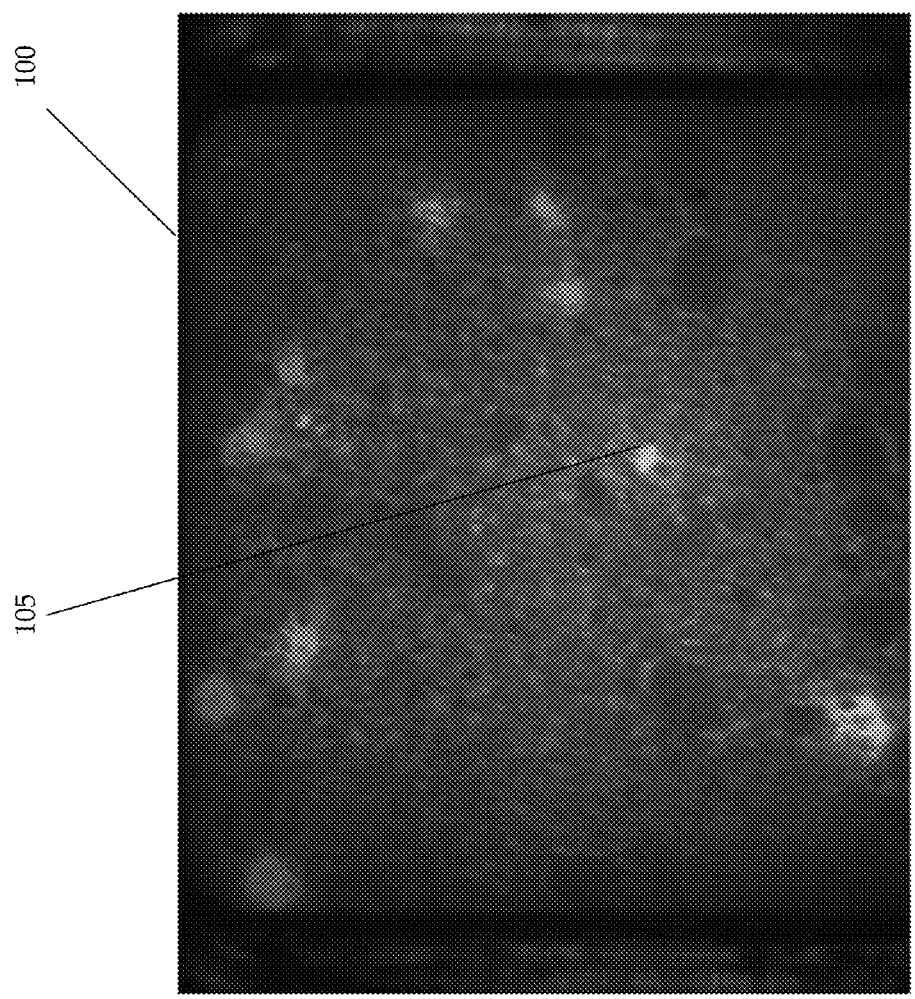
FIG. 1A is an image of a mixture sample that has been illuminated in accordance with the present technology.

In accordance with the present disclosure, the present technology can be used to detect a concentration of Vitamin D particles (e.g., analyte) in CAVD powder. In one embodiment, the CAVD powder is fluoresced at a wavelength of electromagnetic radiation of 405 nanometers. In FIG. 1A, a mixture sample 100 is fluoresced and Vitamin D particles 105 will excite at this wavelength and will begin to glow. The image of FIG. 1A is captured using a system of the present technology, such as the system of FIG. 3, described below. The image of FIG. 1A illustrates a 4000-micron width image of a mixture sample that has been exited with electromagnetic radiation at 405 nanometers. A plurality of Vitamin D particles 105 stand out in luminance magnitude and/or size compared to other components of the mixture sample.

It is noteworthy that Vitamin D is not the only component in CAVD powder that will excite in response to being exposed to electromagnetic radiation at 405 nanometers. For example, CAVD powder may comprise additional analytes that include any of crospovidone, magnesium stearate, and sodium lauryl sulfate, which may all excite to some degree when exposed to electromagnetic radiation at 405 nanometers. Also, contaminates such as paper fibers and other debris may excite at this wavelength. These other analytes may not excite or glow with the same magnitude of luminance as Vitamin D.

Figure 2:
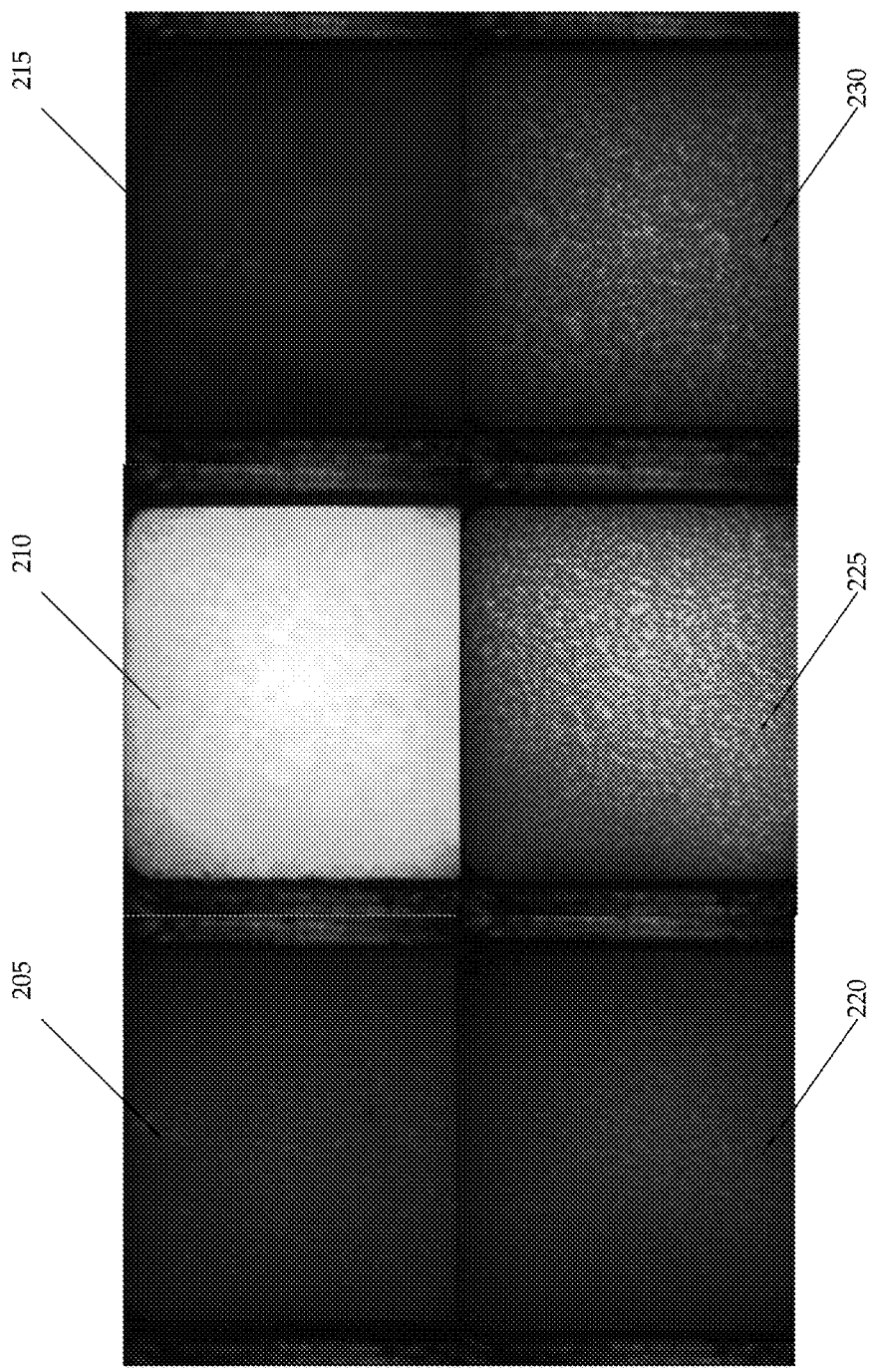
FIG. 2 illustrates several different analytes found in CAVD powder when excited by electromagnetic radiation at 405 nanometers.

Thus, a difference in luminance magnitude can be employed to differentiate between Vitamin D and other analytes in CAVD powder. FIG. 2 illustrates several different analytes found in CAVD powder when excited by electromagnetic radiation at 405 nanometers. Frame 205 is calcium carbonate. Frame 210 is Vitamin D. Frame 215 is magnesium stearate. Frame 220 is microcrystalline cellulose. Frame 225 is crospovione. Frame 230 is sodium lauryl sulfate. It can be seen that Vitamin D has much greater luminance than crospovidone or sodium lauryl sulfate, which are only marginally responsive to electromagnetic radiation at 405 nanometers.

Some contaminates or other analytes may excite with the same magnitude of luminance as Vitamin D analytes. In these instances, the present technology can employ a particle size and/or shape analysis to exclude particles that are not similar in shape and/or size to Vitamin D particles. For reference, Vitamin D particles in this mixture sample are spherical (appearing circular in two dimension views) and approximately 200 to 250 microns across. It will be understood that Vitamin D may be smaller or larger in size than those particles referenced in this example.

In comparison, crospovidone particles are round but smaller than 200 to 250 microns across. In another example, paper fibers are not spherical in shape and can be easily distinguished from Vitamin D particles.

In some embodiments, it is advantageous to filter out fluorescing particles that are not substantially the same size or shape as Vitamin D particles. Thus, these other particles are ignored and not used in the calculation of concentration of Vitamin D, in some embodiments.

Figure 1B:
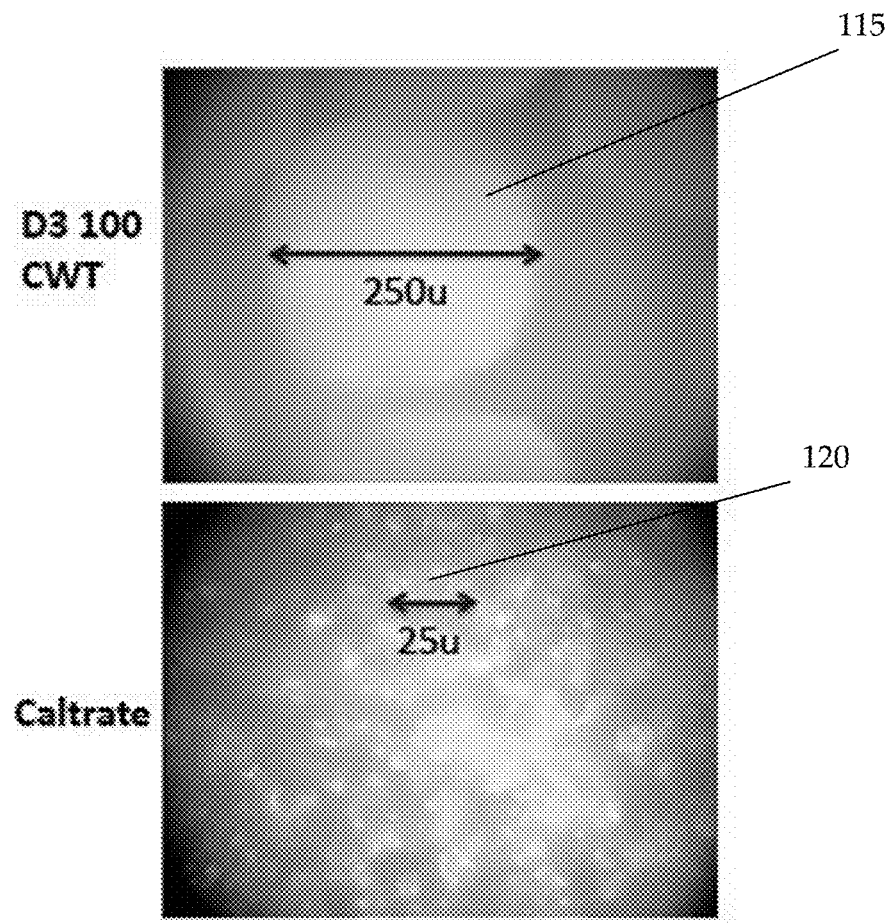
FIG. 1B is an image of a Vitamin D analyte compared to a crospovidone analyte, illustrating a difference in size therebetween.

FIG. 1B is an image of a Vitamin D analyte 115 compared to a CAVD analyte 120, illustrating a difference in size therebetween. For example, the Vitamin D analyte 115 is approximately 250 microns across, whereas the CAVD analyte 120 is approximately 25 microns across.

In sum, the amount of Vitamin D analytes can be determined by viewing particles that glow in the CAVD and excluding other glowing particles that are not substantially circular in shape and approximately 250 microns in size.

The process can include measuring an average amount of "glow" over multiple powder samples (more samples needed for lower concentrations). The process can include employing calibration to convert average "glow" (e.g., responsiveness) to concentration of Vitamin D.

In one embodiment, the three dimensional mapping of particles can be used after the fluoroscopy process used to excite the Vitamin D particles. The three dimensional mapping process described above can be used in combination with the Vitamin D fluoroscopy process to identify and characterize other types matter in the CAVD such as concentrations of other components, contaminates, and other particles. In these processes that use fluoroscopy or other processes that use reflectivity of particles, the size calculation of these particles is not mandatory. A totaling of particles producing a sufficient amount of reflectivity can be used without strict consideration of particle size.

Advantageously, the present technology uses image-processing techniques to analyze chemicals such as powders and emulsions. Image processing is fast and provides first level "triage" for finding Vitamin D3 particles. Image processing is superior to other types of product composition analysis that can take on the order of hours to conduct, as opposed to image processing of the present technology, which can be performed in a fraction of the time.

While detecting Vitamin D particles in CAVD powder is contemplated in some embodiments, the present technology can be used to detect many other types of analytes that are susceptible to excitation with wavelength(s) of electromagnetic radiation.

Figure 3:
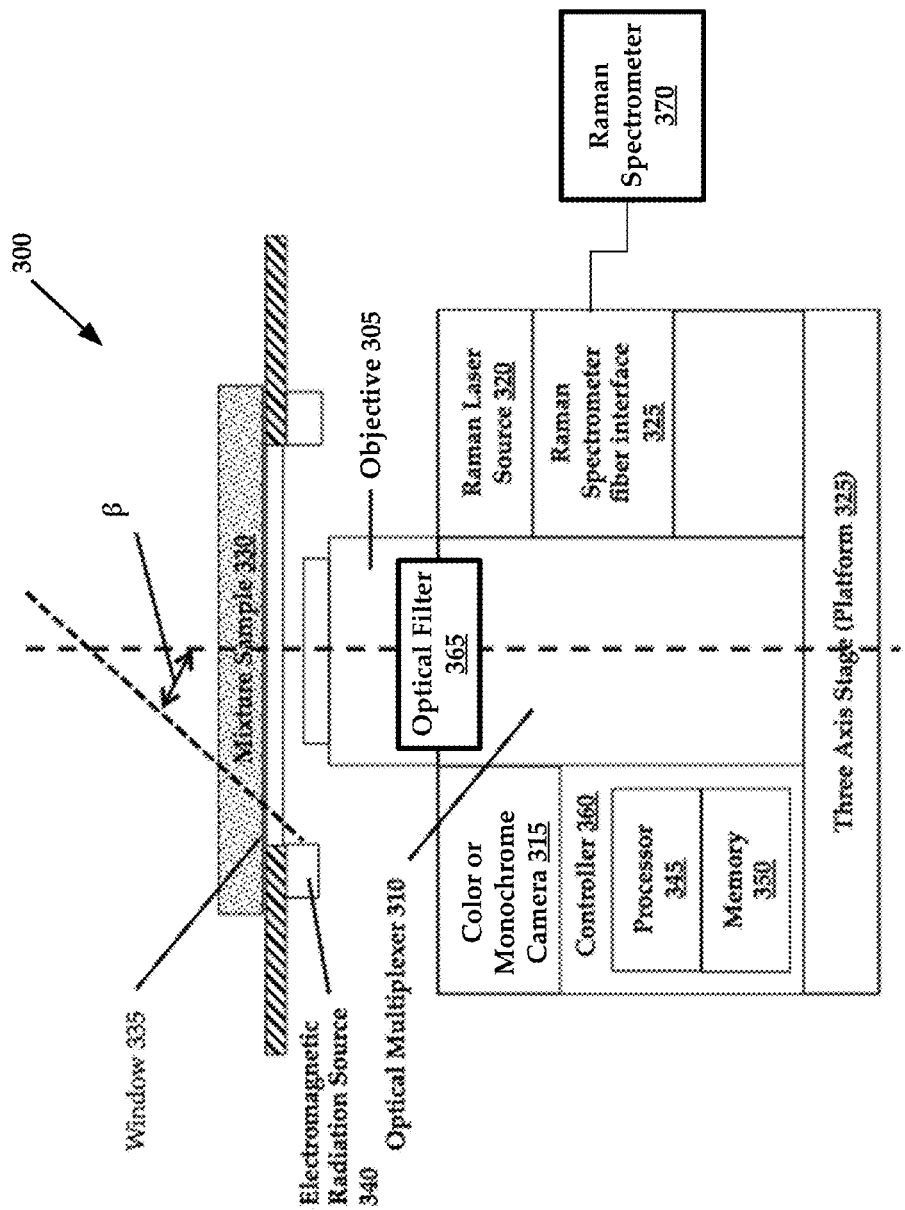
FIG. 3 is an example system for practicing aspects of the present technology.

FIG. 3 is schematic diagram of an example system 300 that can be configured or used to analyze mixture samples. The system 300 comprises an objective 305, an optical multiplexer 310, a color or monochrome camera 315, optional Raman laser source 320, and a Raman spectrometer interface 325, which are all associated with a housing. The housing is mounted on a platform 325 that can move the housing in three axes: X, Y, and Z.

The system 300 can be translated in any of the three directions relative to a mixture sample 330. In some embodiments, the mixture sample 330 is positioned on a transparent or semi-transparent window 335.

An electromagnetic radiation source 340 encircles or lines a perimeter of the window 335 and is configured to emit electromagnetic radiation at the mixture sample 330, exciting analytes in the mixture sample 330. In one embodiment, the electromagnetic radiation source 340 is an electromagnetic radiation ring that is positioned around and below the window 335.

In some embodiments, the system 300 the controller 360 comprises a processor 345 that executes instructions stored in memory 350. The processor 345 and memory 350 can be incorporated into the system 300. In another embodiment, the processor 345 and memory 350 can be located in a control system 360 coupled to the system 300. In FIG. 3, the processor 345 and memory 350 reside on the system 300.

The memory 350 can comprise executable instructions that control the operation of the system 300. For example, the memory 350 can comprise instructions that when executed by the processor 345 causes the electromagnetic radiation source 340 to expose the mixture sample 330 to electromagnetic radiation. The responsiveness (e.g., luminance of light emitted by analytes of the mixture sample 330 in response to excitation) enters the objective 305, passing into the optical multiplexer 310. The system 300 can be configured to use the color or monochrome camera 315 to obtain images of the excited mixture sample, such as the image of FIG. 1.

The controller 360 can employ image analyzing algorithms to: (i) compare particle luminance magnitude; (ii) detect particle size; (iii) compare particle size against other analyte sizes in the mixture sample or to databases of particle sizes; (iv) compare particle size against other analyte shapes in the mixture sample or to databases of particle shapes, and combinations of these algorithms.

In one embodiment, the electromagnetic radiation source 340 emits electromagnetic radiation at a given wavelength of a plurality of wavelengths into the mixture sample 330. It will be understood that electromagnetic radiation source 340 can include, for example, one or more devices that emit electromagnetic radiation within a terahertz range. In another example, a wavelength of the electromagnetic radiation that is used is within a range of approximately 0.01 to 10 nanometers. This range comprises X-ray wavelengths. In yet another embodiment, the electromagnetic radiation that is used is varied in wavelength from blue to ultraviolet light.

In another example, the electromagnetic radiation source 340 emits white light. The responsiveness of the mixture sample is determined by the controller 360 examining color of the one or more of the analytes in the mixture sample.

The electromagnetic radiation source 340 can comprise multiple sources that each provides a unique narrow band wavelength of electromagnetic radiation. For example each of the multiple sources can output any of red, blue, and green light. The multiple sources can include light emitting diodes and lasers.

In yet other embodiments, the electromagnetic radiation source 340 exposes the mixture sample to near infrared or mid infrared light. The electromagnetic radiation output by the electromagnetic radiation source 340 is broad band radiation or successive bursts of narrow bands of radiation. In one embodiment, the electromagnetic radiation source 340 can selectively expose the mixture sample to many different wavelengths of electromagnetic radiation and analyzing how each wavelength affects analytes of the mixture sample. This type of methodology can be advantageous when the system 300 is being used to analyze a mixture sample of unknown composition.

The objective 305 can comprise a high, low, or variable magnification objective lens. The objective 305 can comprise a high magnification lens that allows for viewing of small particles (e.g., less than 20 microns in size). Also, small features can be viewed on larger particles. Low magnification lenses can be used to provide a large field of view, which allows for rapid identification of regions of interest in an image. For example, the image of FIG. 1A would have several regions of interest, such as where groups Vitamin D particles are collocated.

In one embodiment, the magnification of the objective 305 can be selectively varied by the controller 360 to locate particles at low power settings (e.g., magnification). The controller 360 can zoom in where glowing particles are found and execute other analytical processes to identify the particle by shape and/or size, in some embodiments.

In one embodiment, an optical filter 365 can be positioned somewhere prior to the color or monochrome camera 315 to block excitation light because the color or monochrome camera 315 may be sensitive to excitation light. Images obtained by the color or monochrome camera 315, through the optical filter 365, are used for various analyte location and classification processes which are described in greater detail below.

In one embodiment, the optical filter 365 selected for the system 300 will depend upon the wavelength of the electromagnetic radiation that is output by the electromagnetic radiation source 340. Broadly, the optical filter 365 can block light at wavelengths of approximately 425 nanometers to 700 nanometers. Higher wavelength filters are used in combination with, for example, Raman lasers, while lower wavelength filters are used with ultraviolet light.

In one embodiment, the electromagnetic radiation source 340 comprises a 405 nanometer laser and the optical filter 365 comprises a 425 nanometer long pass filter. In another embodiment, the electromagnetic radiation source 340 comprises a 405 nanometer light emitting diode (LED) and the optical filter 365 comprises a 450 nanometer long pass filter. In yet another embodiment, the electromagnetic radiation source 340 comprises a 395 nanometer light emitting diode and the optical filter 365 comprises a 479 nanometer band pass filter with a pass of 40 nanometers or 44 nanometers on either side of 405 nanometers. In general, a laser at 405 nm, an LED at 405, or an LED at 395 nm all have different spectral line widths. Lasers at 405 nanometers have small (narrow) line widths but wide broad bands of amplified spontaneous emission (ASE) compared with an LED at 405 nanometers, which has broad line width but falls off quickly. The LED at 395 nm has very wide band and requires the most blocking in bandwidth.

The various optical filters are used to block the excitation wavelength for the camera. This is because the camera is sensitive to these various excitations wavelengths and would be unable to obtain usable images without filtering. The controller 360 can cause the electromagnetic radiation source 340 to emit electromagnetic radiation for a set period of time, such as ten seconds. Images are captured of the mixture sample by the color or monochrome camera 315 to determine the responsiveness of the mixture sample by detecting timing and decay of response of the one or more of the analytes to the electromagnetic radiation.

As mentioned above the system 300 can use additional measurement algorithms to detect and differentiate analytes in the mixture sample from one another using particle size and shape. For example, the controller 360 of the system 300 can use various image processing methods to determine an aspect ratio for analyte particles Also, the controller 360 of the system 300 can calculate analyte size, shape, fuzziness, angularity, brightness, and combinations thereof.

In one example, the controller 360 can differentiate between Vitamin D and dye particles included in CAVD powder due to the fact that dye particles are usually less than 50 microns in size and irregular in shape, whereas Vitamin D can range in size from anywhere between 75 micrometers to 400 micrometers in size.

The size and/or shape of analytes can be used to detect the presence of paper fibers or other contaminates. For example, if a particle is detected, its size and shape are calculated using image processing. The size and shape can be compared to a database of particle sizes and corresponding shapes. If no reasonable comparison is found, it can inferred that the analyte is a contaminate. Also, manufacturing processes may encounter common foreign particulate matter types. These contaminates can be catalogued and stored in a database.

The algorithm used by the controller 360 can be selected based on the basic composition of the mixture sample, if an expected composition for the mixture sample is known. Thus, the system 300 need to compare analyte responsiveness, size, and/or shape to any and all known particles in the database, but only to those that are reasonably expected to be included in the composition.

In some embodiments, the electromagnetic radiation source 340 can emit electromagnetic radiation into the mixture sample at an angle β that is specified with reference to a central axis C of the window 335. Thus, in some embodiments, the electromagnetic radiation enters the mixture sample at this angle β.

The controller 360 is further configured to count a number of excited particles in the mixture sample. In another embodiment, the controller 360 is further configured to calculate a concentration of a selected analyte. For example, when the controller 360 has located a number of Vitamin D analytes in the mixture sample, the controller 360 can calculate a volume of Vitamin D analytes in the mixture sample using image analysis. The overall area of the particles of Vitamin D relative to the total area of the image can be used to estimate the volume by weight of Vitamin D, if the size of the Vitamin D particles is known.

According to some embodiments, the presence, size, and/or shape of analytes such as Vitamin D can be verified using Raman spectroscopy. In one embodiment, the optional Raman laser source 320 is controlled by the controller 360 to expose the mixture sample to a wavelength of laser light. The laser light can be focused onto a small portion of the mixture sample where candidate particles are fluorescing (e.g., responsive). Images are transferred by the optical multiplexer 310 to the Raman spectrometer interface 325. It will be understood that the Raman spectrometer interface 325 is coupled to a Raman spectrometer 370, which can be integrated into the system 300 or in a standalone configuration. The identification of the candidate particles are confirmed using Raman spectroscopy. While a Raman laser source has been described, it will be understood that the system 300 can include X-ray, near infrared, infrared sources, as well as other sources of electromagnetic radiation. To be sure, the system 300 can include combinations or permutations of these electromagnetic radiation sources, depending on the type of products being analyzed.

In some embodiments, the system 300 can be used to obtain three dimensional models of the mixture sample. A three dimensional model is a composition of many images obtained using permutations of positions in the three axes X, Y, and Z.

In one embodiment, the objective lens 305 (due to translation of the housing using the platform 325) is translatable in three axes X, Y, and Z. The Z-axis is aligned with the central axis C of the window 335.

Depending on the width of the field of view of the color or monochrome camera 315, the objective lens 305 is moved sequentially along the window 335 in the X and Y direction. At each X and Y location, the platform 325 will translate the objective lens 305 from an initial position along the Z-axis towards the window 335, in one micron increments. At each one micron increment, the color or monochrome camera 315 obtains an image of the illuminated mixture sample. The system 300 is capable of obtaining images at any given depth into the mixture sample. These images are each associated with their respective X, Y, and Z location information. The images can be assembled together by the system 300 to form a three-dimensional model of the mixture sample.

Figure 4:
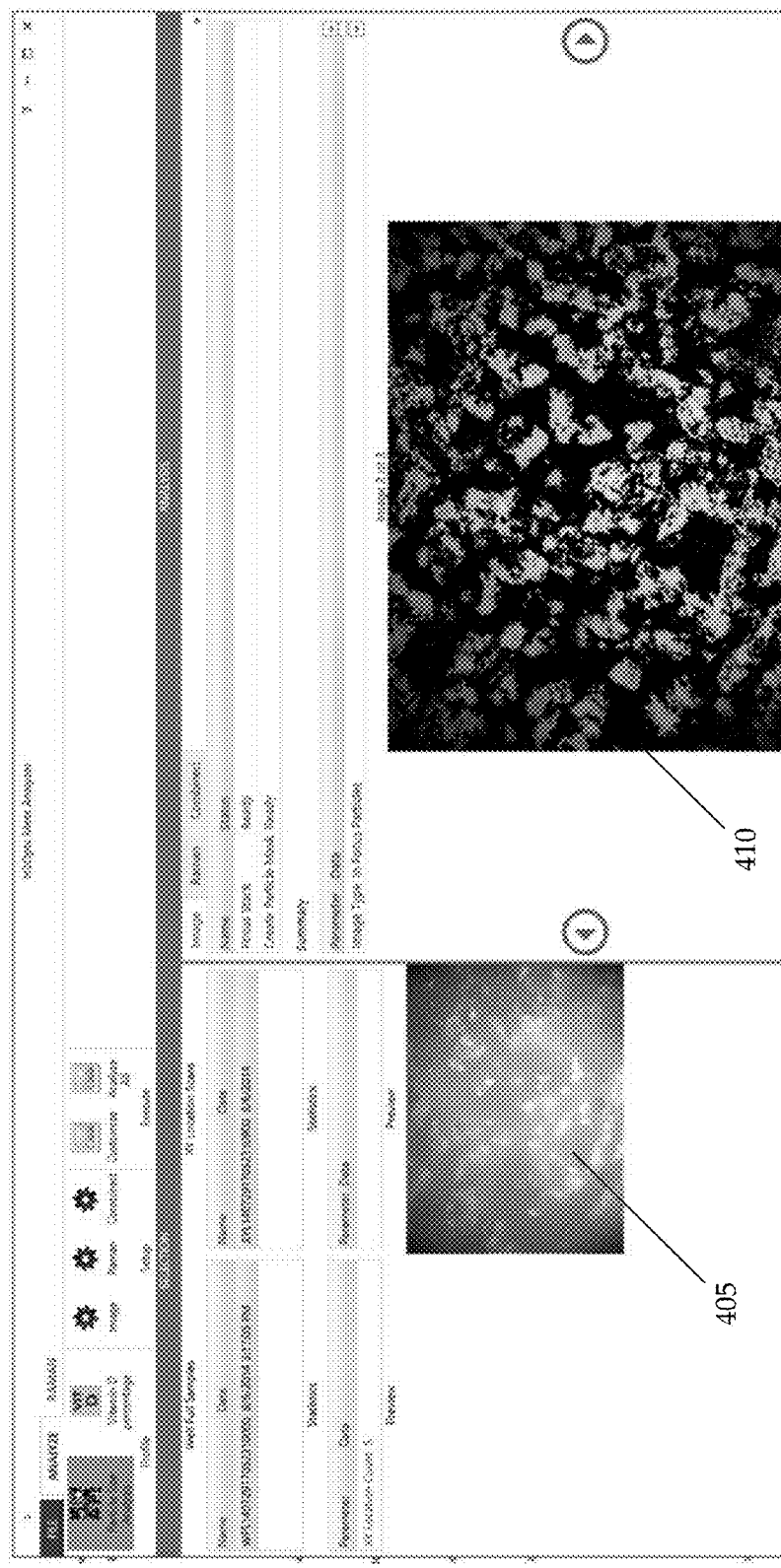
FIG. 4A is an example image of a mixture sample.
FIG. 4B is an example three dimensional model that incorporates the mixture sample image of FIG. 4A.

In FIG. 4A, a single image 405 of a mixture sample is shown. In comparison, FIG. 4B illustrates a three-dimensional model 410 generated using the image 405 of FIG. 4A, as well as a plurality of other images obtained of the same mixture sample at other X, Y, and Z locations.

Figure 5:
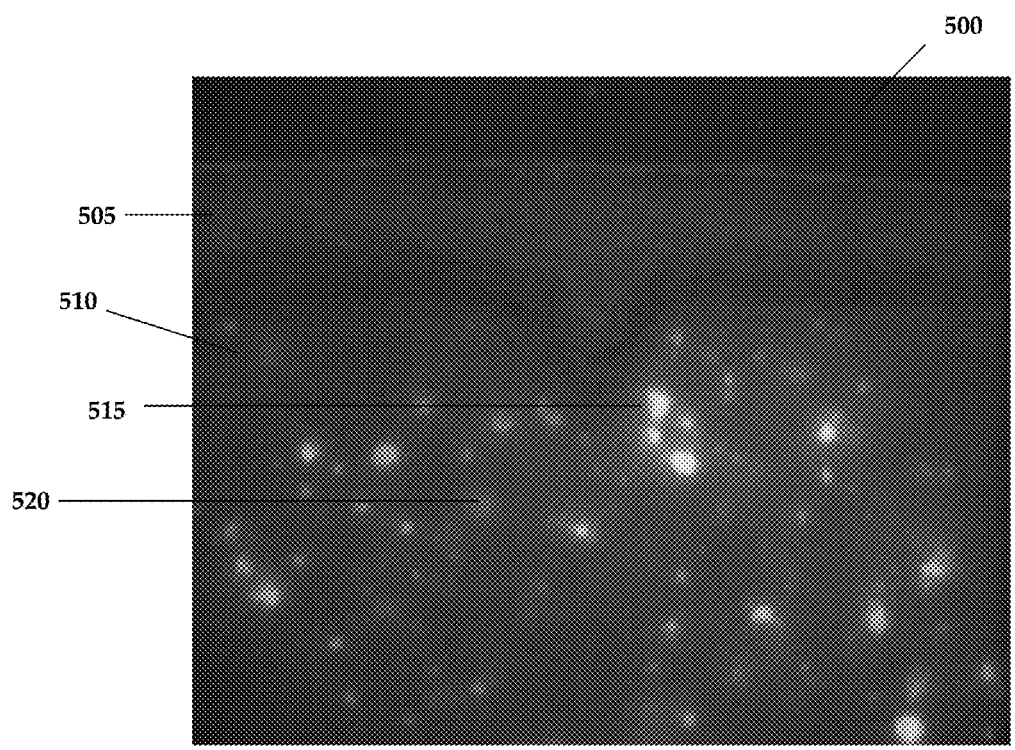
FIG. 5 is a partial cross sectional view of a CAVD tablet that has been illuminated with electromagnetic radiation.

In some embodiments, the three-dimensional imaging of a mixture sample can be used to calculate responsive analyte particles on a surface of the mixture sample, as well as particles located within the mixture sample at a specified distance inside the surface of the mixture sample. In some embodiments, this process can be accomplished by scraping or cutting the mixture sample; an example process is illustrated in FIG. 5.

In another embodiment, the system can calculate an aggregate of a number of particles on the surface and particles located within the mixture sample at the specified distance inside the surface of the mixture sample.

In yet another embodiment, the system 300 can be configured to verify an accuracy of concentration of an analyte (such as Vitamin D) that was calculated using a number of responsive analyte particles located within the mixture sample at the specified distance inside the surface of the mixture sample. In another embodiment, system 300 can be configured to verify an accuracy of concentration of an analyte using an aggregate of a number of particles on the surface and particles located within the mixture sample at the specified distance inside the surface of the mixture sample. Again, this total or aggregate can be calculated using a three-dimensional mode of the mixture sample.

In an example use case, an uncoated CAVD tablet is imaged using the system 300 of FIG. 3. The system 300 uses an ultraviolet light emitting diode or laser, which is tuned to 405 nanometers. The uncoated CAVD tablet is illuminated with the UV diode or laser. The system 300, using the image, calculates an area of the tablet that comprises Vitamin D directly on the surface of the CAVD tablet. Again, this is possible because the Vitamin D fluoresces in the presence of the UV light.

Raman spectroscopy can be used to confirm the presence of Vitamin D.

Next, the system 300 uses a calibration curve or first principles to relate an area of coverage of the Vitamin D to concentration. In some embodiments, the system 300 employs multiple calibrations and compares the outcome to one another for consistency.

Next, the method comprises shaving the CAVD tablet at one or more planes and repeating the above processes to further confirm the accuracy of the concentration value of the Vitamin D calculated from the surface Vitamin D.

As is illustrated in FIG. 5, a partial cross sectional view of a CAVD tablet 500 is illustrated. A coating 505 is shown, as well as a mixture sample 510 inside the coating 505. Surface Vitamin D particle 515 can be seen. The surface Vitamin D particle 515 is more luminous (e.g., responsive) than the surrounding composition. Also illustrated is a sub-surface Vitamin D particle 520. The sub-surface Vitamin D particle 520 is less luminous than the surface Vitamin D particle 515.

The sub-surface Vitamin D particle 520 can be confirmed as Vitamin D using Raman spectroscopy (if needed). In another example, the sub-surface Vitamin D particle 520 is verified as Vitamin D due to the size and shape similarity between the surface Vitamin D particle 515 and the sub-surface Vitamin D particle 520.

Figure 6:
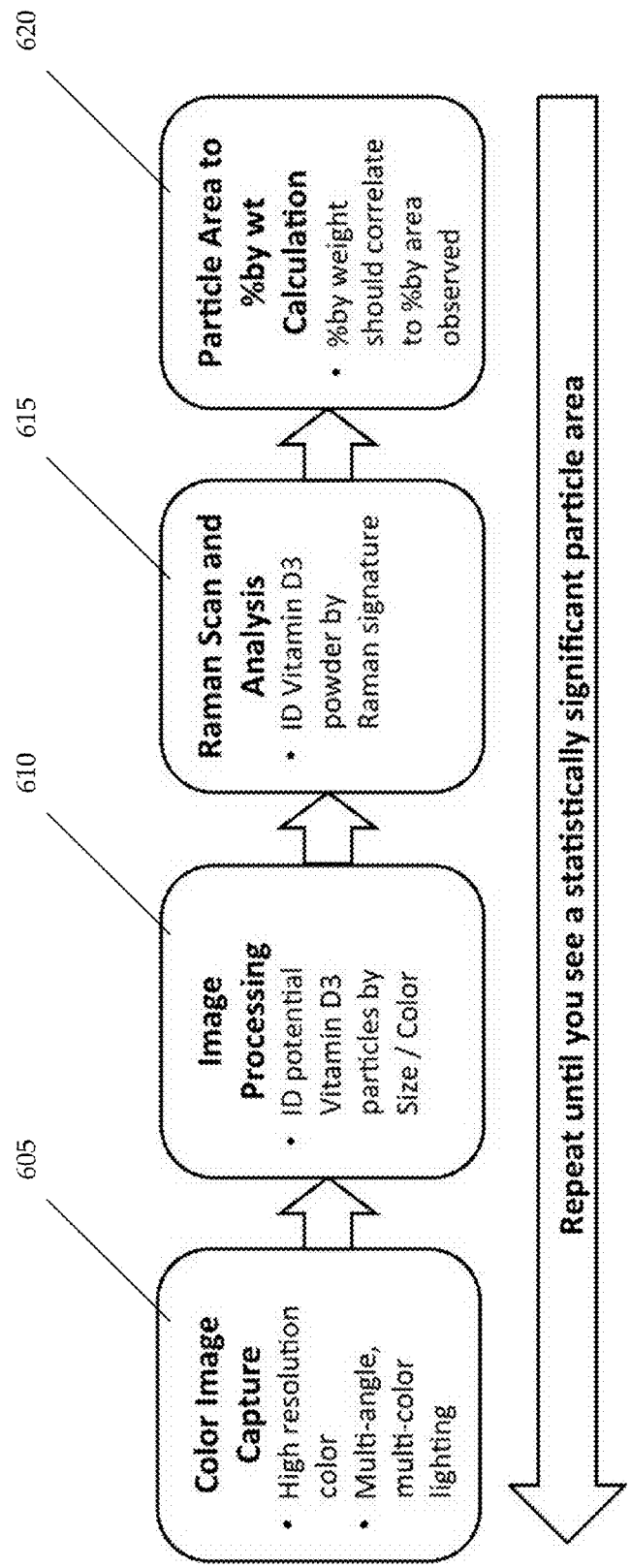
FIG. 6 is a flow diagram of an example method for analyzing mixture samples that comprise Vitamin D.

FIG. 6 illustrates a flow diagram of an example method for analyzing mixture samples that comprise Vitamin D. The process begins with capturing 605 high resolution color images of a mixture sample that is exposed with multiple color lighting (e.g., a range of wavelengths of electromagnetic radiation). The multiple color lighting of the mixture sample occurs at multiple angles. For example, the angle β (see FIG. 3) can be selectively varied during illumination of the mixture sample.

The process also includes processing 610 of the images to identify possible Vitamin D particles by size, color, and/or shape. The process includes using Raman 615 scanning and analysis to positively identify candidate particles as Vitamin D. This can be accomplished using a Raman signature for Vitamin D as a baseline.

The process also includes calculating 620 a particle area to percentage-by-weight calculation where a percentage-by-weight is correlated to a percentage-by-area of Vitamin D particles observed in the images.

It will be understood that the process of FIG. 6 can be repeated until a statistically significant particle area is located in one or more mixture samples.

EXAMPLE 1

Figure 7:
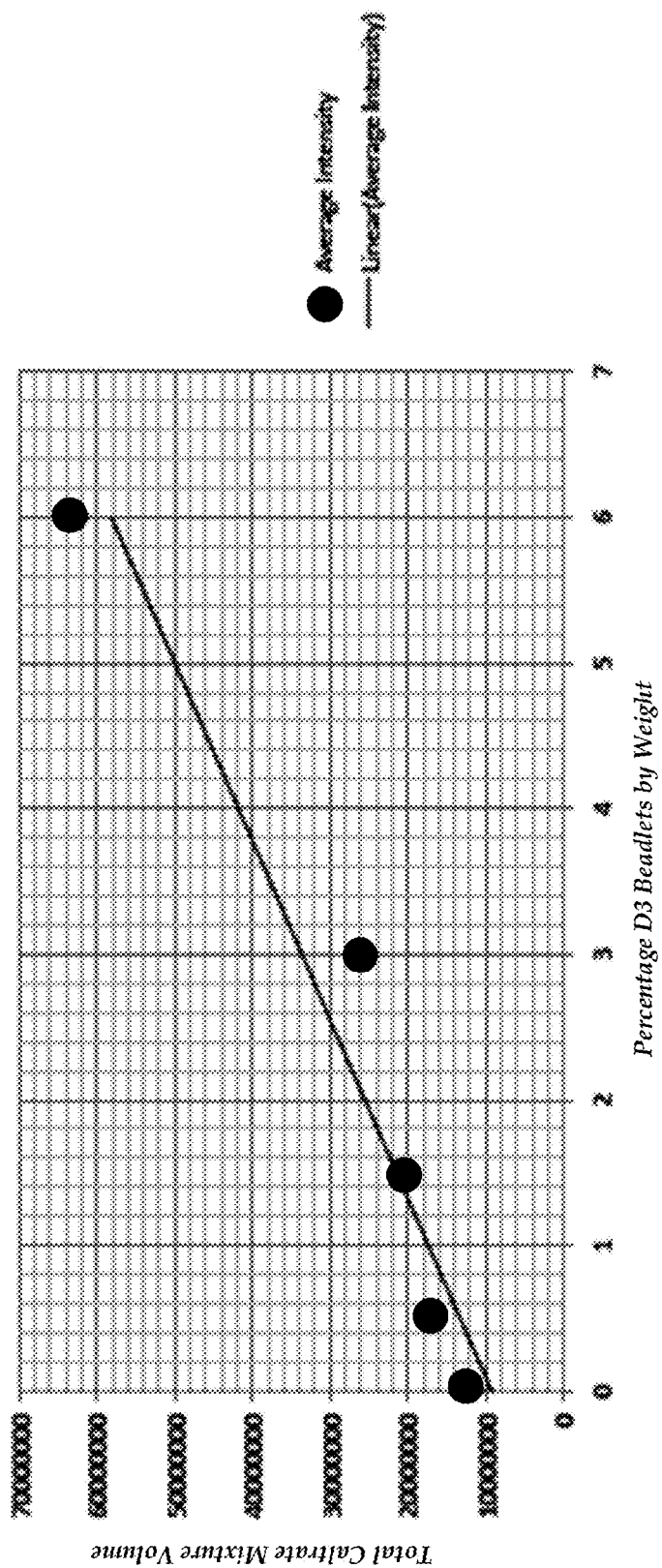
Figure 8:
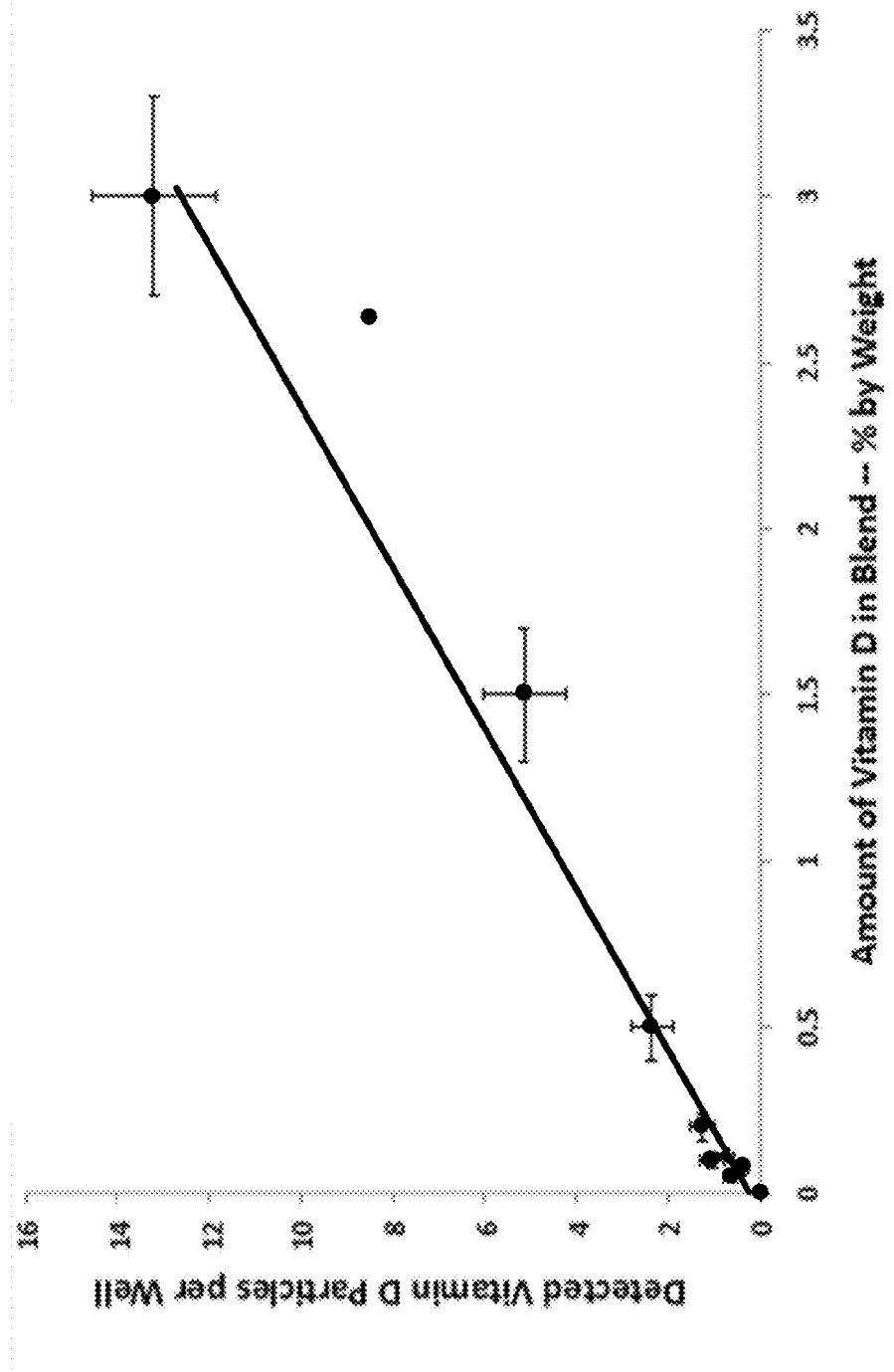

Referring now to FIGS. 7-9, collectively, a plurality of samples of CAVD mixture were analyzed using a fluoroscopy processes, similar to the process described above that utilized electromagnetic radiation at 405 nanometers in wavelength. The process was used to calculate the average intensity of Vitamin D3 beadlets in various volumes of CAVD mixture. In FIG. 7, a graph is shown, illustrating a total volume of CAVD mixture in the Y-axis and a percentage of D3 beadlets by weight on the X-axis.

For context, a total of ten samples of each of five concentrations of CAVD, which included Vitamin D3, were analyzed.

For each sample volume of CAVD mixture, it can be seen that the percentage of Vitamin D3 beadlets increases with the size of the CAVD mixture volume. More specifically, the average image intensity (luminance) scales directly with beadlet concentration in the CAVD samples, for test blends of 0.5% up to 20% (note that blends of up to 7% are shown).

The points illustrated on the graph are an average luminance intensity that was detected in the samples, where luminance of Vitamin D3 analytes was correlated to overall volume of the CAVD mixture. A line of average luminance can be placed onto the graph, illustrating the generally linear/proportional increase in Vitamin D3 beadlets per increasing volume of CAVD powder.

In FIG. 8, another graph is illustrated, showing a relationship between the amount of detected Vitamin D particles per sample of CAVD mixture (e.g., per Well), where the Well is the amount of CAVD powder that is disposed on the window of FIG. 3. The amount of detected Vitamin D particles per sample of CAVD mixture is shown in correlation to an amount of Vitamin D in the CAVD mixture sample, expressed as a percentage by weight of Vitamin D. The sample data points are plotted on the graph. Again, a linear relationship is seen. Training test data points are illustrated as circles, and the final test blend is represented as a triangle. A trend line representing the test data points is overlaid on the graph, showing the linear and somewhat proportional nature of the data.

The present technology can employ various equations in calculating the area and volume of analytes in a mixture sample. The volume percentage of vitamin D analytes in a mixture sample is calculated using:

$$\text{Cross Sectional Area} = (2\pi r^2)/3 \qquad \text{(Equation 1)}$$

Equation 1 can be used to calculate the Cross Sectional Area of vitamin D in a layer of a sample, such as when a tablet is scraped and evaluated using the present technology. It will be understood that m=1 for a single layer calculation. Equation 1 is derived using an average cross sectional area of a slice of a sample. When a slice is taken, vitamin D particles may be intersected through the middle (largest radius value) or towards the bottom (lower radius value), and anywhere in between the middle and ends.

The area percentage calculated from Equation 1 is equivalent to a volume percentage. Furthermore, it is noteworthy that the area percentage is equivalent to the volume percentage, because these calculations are not a direct function of the r (radius). The r (radius) is variable in Equation 1. Equation 1 was used to calculate the data of FIG. 9. A vitamin D area to weight relationship was also determined by calculating a density of both calcium supplement and vitamin D, both being analytes in a mixture. In one instance, 2.2 milliliters of vitamin D particles in a test tube, which weighed 1.427 grams. Since the vitamin D is a particulate, it was preferred to confirm this weight using water. Thus, 2.25 milliliters of water was added to the vitamin D particles, which weighed 2.081 grams.

The density of water is calculated as 0.925 (it is assumed to be one (1)). Thus, the density of vitamin D is 0.649, assuming water has a density of 1. Empirically, the vitamin D had a density of 0.649/0.925 which is 0.701. The same calculations can be used to determine the density of a mixture sample. The density of the mixture sample, divided by the density of the vitamin D can is used to calculate a scale value using a comparison of weight and volume fractions. For example, if the density of the mixture sample is 0.930, the scale value can be determined by dividing the density of the mixture sample by the density of the vitamin D, for a scale value of 4/3. Thus, the vitamin D by volume will appear more numerous than the actual weight percentage. For example, vitamin D by weight will be 0.11% while the percentage of vitamin D by volume is 0.145%. In the table data of FIG. 9, various calculations are illustrated for the test data described above. In detail, the well floor area was 16000000 square microns in size. The total Vitamin D area, based on a volume percentage is 40148 square microns. An expected number of Vitamin D particles in any given well were 1.28.

The system of FIG. 3 was used to determine various attributes of Vitamin D particles using the present technology. An observed diameter (e.g., average diameter) of the Vitamin D particles was 200 microns, which gave a radius of 100 microns. A calculated projected area was 31416 square microns using an area of a circle calculation. Additionally, an average volume of each Vitamin D particle is calculated to be 4188790 microns cubed. A density of the Vitamin D was calculated using PEG6000 (polyethylene glycol). The density of the Vitamin D was 1.08 grams per cubic centimeter.

The system also differentiated between the Vitamin D and calcium carbonate in the CAVD samples. The density of the calcium carbonate was 2.71 grams per cubic centimeter.

An approximate mass percentage of Vitamin D in each CAVD sample was determined to be 0.1%, while the mass percentage of calcium carbonate (and other analytes) was determined to be 99.9%.

A density ratio of calcium carbonate to Vitamin D was calculated to be 2.50925926, while a nominal volume of Vitamin D was found to be 0.2509256. A total reference volume for the CAVD samples was 100.150926, which resulted in the calculation of Vitamin D by volume of 0.25054778% and calcium carbonate by volume of 99.75%.

Figure 10A:
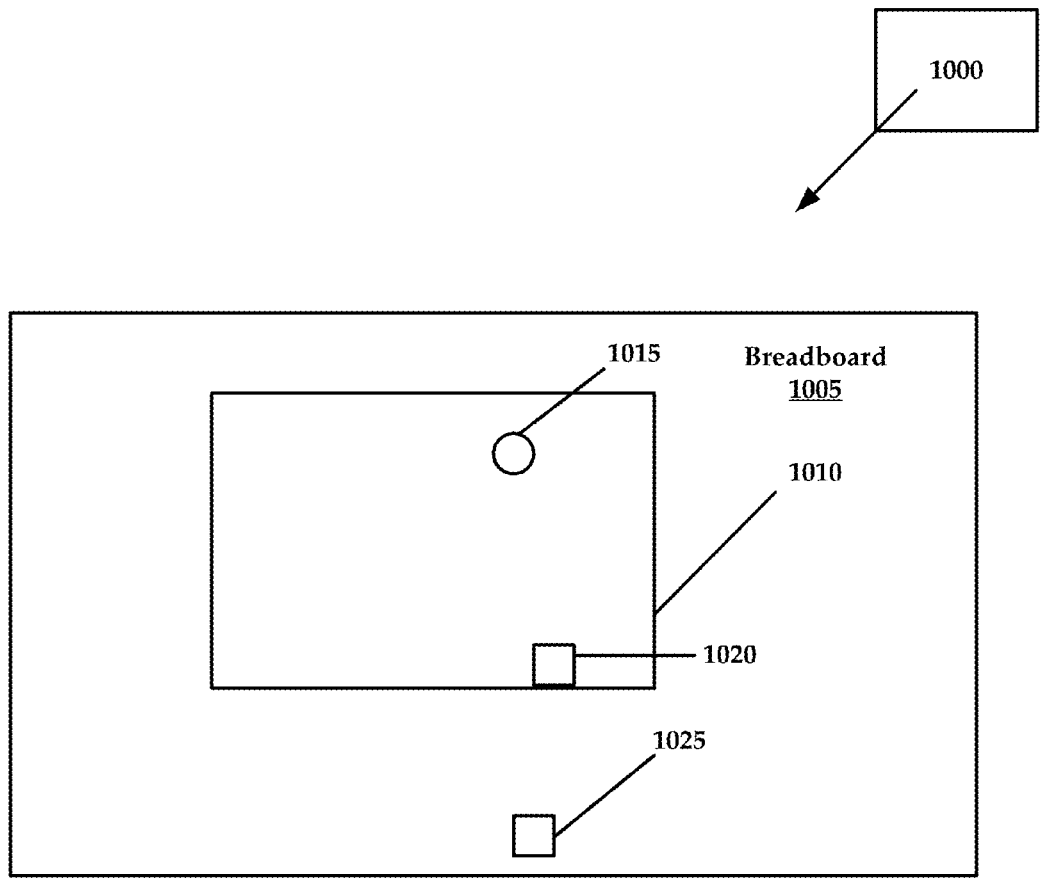
FIG. 10A is a schematic diagram of an example system that can be used to detect analytes in a mixture sample.

FIG. 10A is an embodiment of another system 1000 that can be used to analyze mixture samples. The system 1000 comprises a breadboard 1005, a shrouded box 1010, a vial 1015, a UV source 1020, and a camera with a filter 1025.

The breadboard 1005 serves as a mounting surface for the shrouded box 1010. The vial 1015 is placed into the shrouded box 1010 and illuminated with the UV source 1020. The UV source can include any suitable UV source tuned to approximately 405 nanometers. The UV source can be a laser or a light emitting diode. As mentioned above, the filter used in combination with the UV source is selected based on the excitation wavelength of the UV source.

Figure 10B:
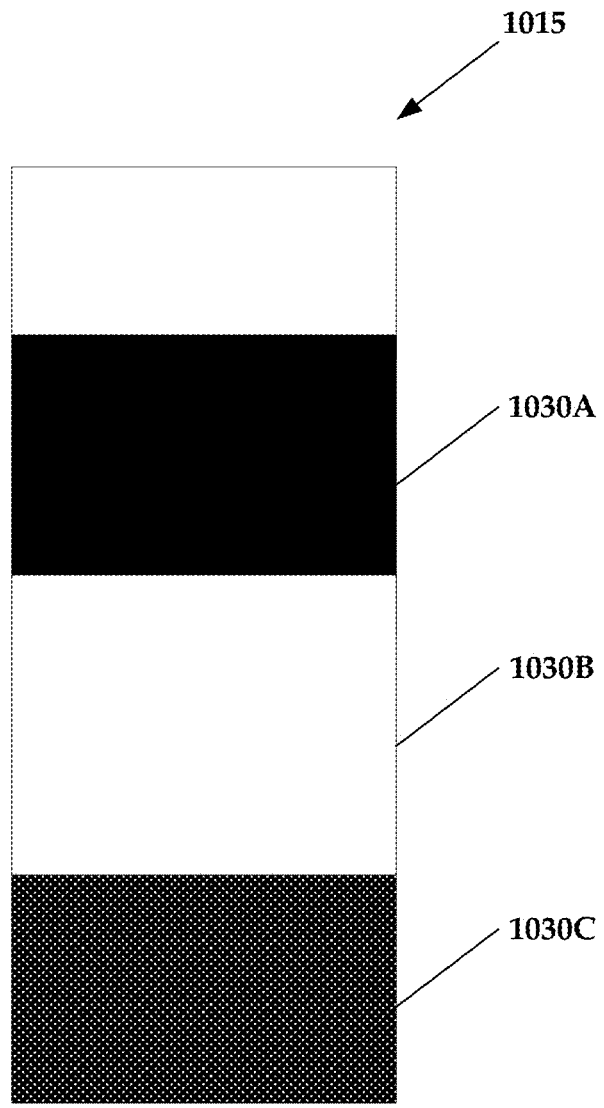
FIG. 10B is a cross sectional view of a vial that includes layers of compositions.

FIG. 10B is a cross section view of a vial that includes three layers 1030A-C. Layer 1030A is pure calcium carbonate, layer 1030B is a layer of vitamin D particles, and layer 1030C is a mixture sample that comprises calcium carbonate supplemented with vitamin D particles. The vial has been exposed to UV light at 405 nanometers. Layer 1030A is completely non-reactive. Layer 1030B is highly reactive and layer 1030C is reactive in proportion to the amount of vitamin D included in the mixture sample.

For context, when measurements of luminance of vitamin D particles are measured using the present technology it is noted that individual particles will radiate or excite with a lower luminance level compared to clusters of vitamin D particles that are spaced apart from one another. This feature is due to the fact that the particles will produce radiated light which is combined with reflected light from adjacent particles. It was determined that a single vitamin D particle has a lower contrast 2:1 than clustered particles. In one experiment with the system 1000, a UV light of 405 nanometers was used in combination with a long pass filter. A 425 nanometer long pass filter required an LED cleanup filter for examining calcium carbonate, but not for a mixture sample. In another experiment a 405 nm UV light was used with a 479 nanometer bandpass filter with a 40 nm bandpass filter and did not require any cleanup filtering because the passband was sufficiently removed from the 405 nm center wavelength so that very little of the UV excitation light was transmitted by the filter.

Figure 11:
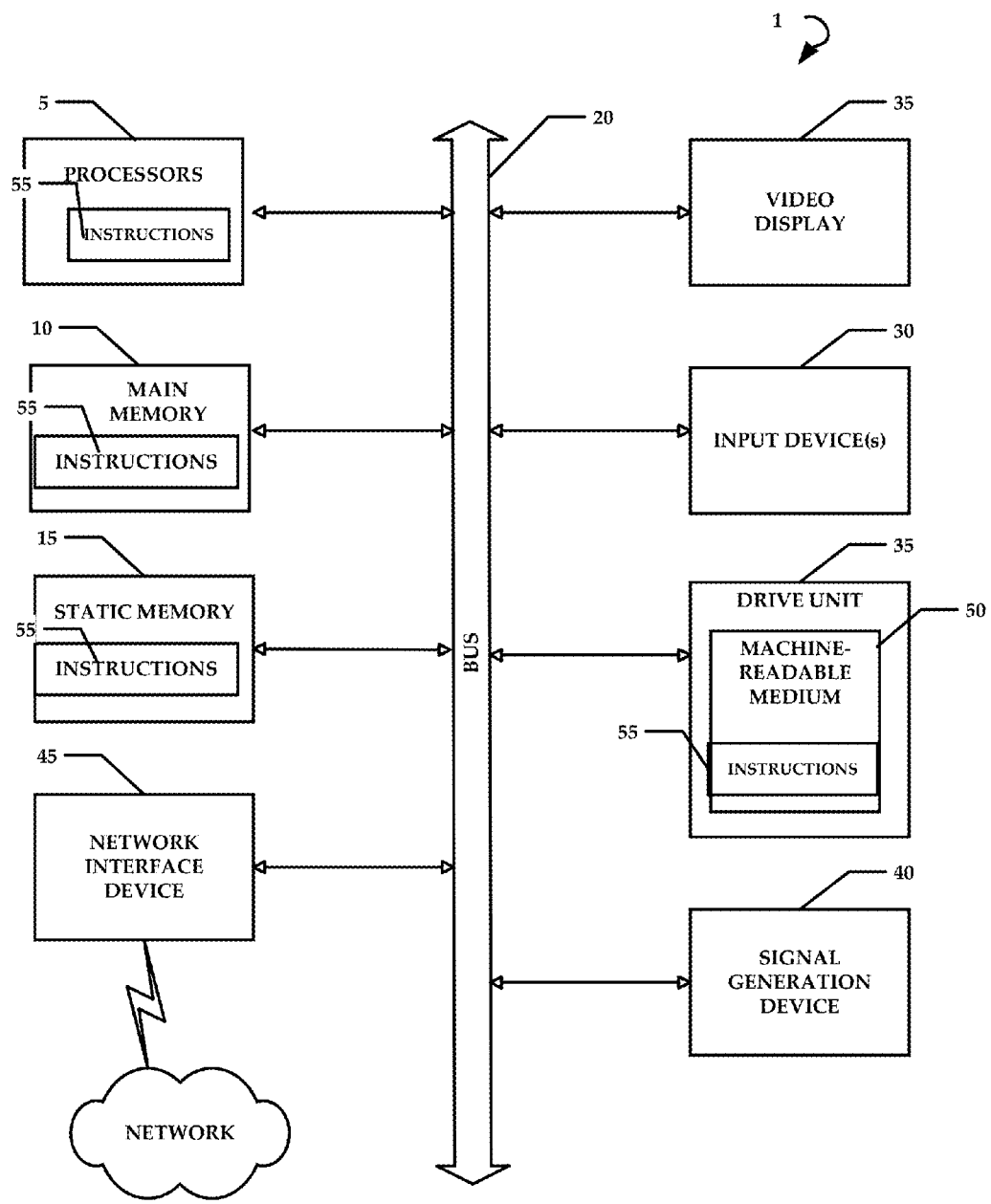
FIG. 11 is an example machine that can be used to implement aspects of the present technology.

Embodiments of the present technology may make use of computing systems such as the computing system of FIG. 11. Generally, the algorithms mentioned herein can be stored in memory and executed by a processor to perform the methods and/or processes described herein.

FIG. 11 is a diagrammatic representation of an example machine in the form of a computing system 1, within which a set of instructions for causing the machine to perform any one or more of the methodologies discussed herein may be executed. The computing system 1 can be used as the controller 360 of FIG. 3, where the controller 360 is configured to perform the methods and processes described herein by storing instructions in memory and executing those instructions with a processor.

In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a personal digital assistant (PDA), a cellular telephone, a portable music player (e.g., a portable hard drive audio device such as an Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computing system 1 includes a processor or multiple processors 5 (e.g., a central processing unit (CPU), a graphics processing unit (GPU), or both), and a main memory 10 and static memory 15, which communicate with each other via a bus 20. The computing system 1 may further include a video display 35 (e.g., a liquid crystal display (LCD)). The computing system 1 may also include an alpha-numeric input device(s) 30 (e.g., a keyboard), a cursor control device (e.g., a mouse), a voice recognition or biometric verification unit (not shown), a drive unit 35 (also referred to as disk drive unit), a signal generation device 40 (e.g., a speaker), and a network interface device 45. The computing system 1 may further include a data encryption module (not shown) to encrypt data.

The disk drive unit 35 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processors 5 during execution thereof by the computing system 1. The main memory 10 and the processors 5 may also constitute machine-readable media.

The instructions 55 may further be transmitted or received over a network via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

One skilled in the art will recognize that the Internet service may be configured to provide Internet access to one or more computing systems that are coupled to the Internet service, and that the computing systems may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the disclosure as described herein.

In the following description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It is noted at the outset that the terms "coupled," "connected", "connecting," "electrically connected," etc., are used interchangeably herein to generally refer to the condition of being electrically/electronically connected. Similarly, a first entity is considered to be in "communication" with a second entity (or entities) when the first entity electrically sends and/or receives (whether through wireline or wireless means) information signals (whether containing data information or non-data/control information) to the second entity regardless of the type (analog or digital) of those signals. It is further noted that various figures (including component diagrams) shown and discussed herein are for illustrative purpose only, and are not drawn to scale.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. A method for detecting a concentration of an analyte in a mixture sample, the method comprising:
    exposing a mixture sample to electromagnetic radiation, the mixture sample comprising one or more analytes, wherein exposing the mixture sample to electromagnetic radiation comprises exposing the mixture sample to near infrared, mid infrared light, or ultraviolet light, wherein the electromagnetic radiation is broad band or successive narrow bands;
    detecting responsiveness of one or more of the analytes to the electromagnetic radiation;
    calculating average responsiveness of the one or more of the analytes; and
    calculating a concentration of the one or more of the analytes in the mixture sample using the average responsiveness, wherein calculating a concentration further comprises counting each responsive analyte and calculating a size and shape of each of each responsive analyte.

2. The method according to claim 1, further comprising using Raman spectroscopy to confirm the presence of the one or more of the analytes in the mixture sample.

3. The method according to claim 1, further comprising performing the method of claim 1 on a plurality of mixture samples from a batch to calculate a batch concentration of the one or more of the analytes in the batch.

4. The method according to claim 1, wherein a spectrum of the electromagnetic radiation is varied in wavelength from blue to ultraviolet.

5. The method according to claim 1, wherein exposing comprises exposing the mixture sample to electromagnetic radiation for a set period of time, further wherein responsiveness comprises detecting timing and decay of a response of the one or more of the analytes to the electromagnetic radiation.

6. The method according to claim 1, wherein a wavelength of the electromagnetic radiation corresponds to white light and the responsiveness is determined by examining color of the one or more of the analytes.

7. The method according to claim 1, wherein the electromagnetic radiation is generated from multiple sources that each provide a unique narrow band wavelength of electromagnetic radiation, the multiple sources comprising any of red, blue, and green light emitting diodes and lasers.

8. The method according to claim 1, wherein counting each responsive analyte comprises counting each response analyte on a surface of the mixture sample and counting each responsive analyte located within the mixture sample at a specified distance inside the surface of the mixture sample.

9. The method according to claim 8, further comprising calculating an aggregate of a number of responsive analytes on the surface and responsive analytes located within the mixture sample at the specified distance inside the surface of the mixture sample.

10. The method according to claim 9, further comprising verifying accuracy of concentration calculated using a number of responsive analytes using at least one of:
a number of responsive analytes located within the mixture sample at the specified distance inside the surface of the mixture sample; and
an aggregate of a number of responsive analytes on the surface and responsive analytes located within the mixture sample at the specified distance inside the surface of the mixture sample.

11. The method according to claim 1, wherein the one or more of the analytes comprises Vitamin D and the mixture sample is a calcium supplement that comprises Vitamin D particles.

12. The method according to claim 1, further comprising filtering out other responsive analyte particles of the one or more of the analytes that are not substantially the same size or shape as Vitamin D particles.

13. A method, comprising:
fluorescing a plurality of samples of a calcium supplement that comprises Vitamin D particles;
for each of the plurality of samples of the calcium supplement that comprises Vitamin D particles, locating analytes that fluoresce at 405 nm;
determining what part of the analytes are Vitamin D; and
calculate average fluorescence of the Vitamin D over the plurality of samples to determine the concentration of Vitamin D in the plurality of samples of the calcium supplement that comprises Vitamin D particles.

14. The method according to claim 13, further comprising using Raman spectroscopy to confirm the presence of Vitamin D particles; and filtering out fluorescing particles that are not substantially the same size or shape as Vitamin D particles.

15. The method according to claim 13, wherein determining what part of the analytes are Vitamin D comprises counting fluorescing analyte particles that have a size and shape that correspond to the size and shape of Vitamin D particles.

16. A method, comprising:
capturing high resolution images of a mixture sample of a powdered calcium supplement that comprises Vitamin D particles using multiple wavelengths of light, wherein the multiple wavelengths of light are directed to the mixture sample at different angles;
processing the high resolution images to identify possible Vitamin D particles by size, color, and shape;
conducting a Raman spectroscopic analysis of the possible Vitamin D particles to confirm identification of the Vitamin D particles; and
calculating a particle area to percentage-by-weight value where a percentage-by-weight is correlated to a percentage-by-area of Vitamin D particles observed in the high resolution images.

* * * * *